United States Patent [19]

Henrick

[11] 4,223,033

[45] Sep. 16, 1980

[54] SUBSTITUTED PYRIDINE METHYL ESTERS OF NAPHTHYL ACIDS

[75] Inventor: Clive A. Henrick, Palo Alto, Calif.

[73] Assignee: Zoecon Corporation, Palo Alto, Calif.

[21] Appl. No.: 69,446

[22] Filed: Aug. 24, 1979

[51] Int. Cl.³ .................... C07D 213/55; A61K 31/44
[52] U.S. Cl. .................................. 424/263; 546/300;
546/301; 546/302; 546/314; 546/333
[58] Field of Search .............. 546/300, 301, 302, 314, 546/333; 424/263

[56] References Cited

U.S. PATENT DOCUMENTS

| | | | |
|---|---|---|---|
| 4,173,637 | 11/1979 | Nishiyama et al. | 546/300 |
| 4,173,638 | 11/1979 | Nishiyama et al. | 546/300 |

Primary Examiner—Alan L. Rotman

[57] ABSTRACT

Pyridyl esters and thiolesters of naphthyl acids, intermediates therefor, synthesis thereof and the use of said esters and thiolesters and compositions for the control of pests.

21 Claims, No Drawings

SUBSTITUTED PYRIDINE METHYL ESTERS OF NAPHTHYL ACIDS

This invention relates to novel esters and thiolesters of α-substituted saturated acids, novel intermediates therefor, synthesis thereof, and the control of pests.

The esters and thiolesters of the present invention are represented by the following formula (A):

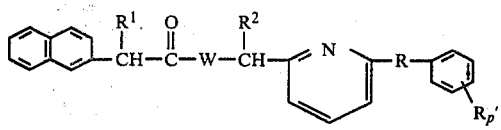

wherein,
W is oxygen, or sulfur;
p is zero, one or two;
R is oxygen, sulfur, methylene or carbonyl;
R' is fluoro, bromo, chloro, trifluoromethyl, methyl, methoxy or methylthio;
$R^1$ is lower alkyl of 2 to 5 carbon atoms;
$R^2$ is hydrogen, cyano, ethynyl, methyl, trifluoromethyl or thioamide; and the salt thereof of a strong inorganic acid or organic acid.

The compounds of the present invention represented by formula (A) are useful agents for the control of pests such as insects and acarids.

In the description hereinafter and the appended claims, each of R through $R^2$, W, and p is as defined hereinabove, unless otherwise specified.

The compounds of formula (A) can be synthesized as outlined below.

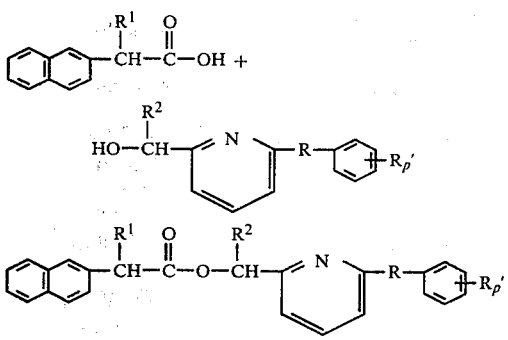

In the general practice of the above synthesis, an acid, salt thereof or the acid chloride is reacted with an alcohol of formula II to form the carboxylic ester A'. For example, an acid chloride of the acid of formula I is reacted with an alcohol of formula II in an organic solvent such as diethyl ether in the presence of triethylamine. In another embodiment, an acid of formula I and an alcohol of formula II are reacted in an organic solvent such as methylene chloride in the presence of 4-dimethylaminopyridine and dicyclohexylcarbodiimide to form an ester of formula A'. In another synthesis, the acid of formula I or salt thereof is reacted with the bromide, chloride or mesylate of the alcohol for formula II to form an ester of formula A'. The starting materials of formula I can be made as described by Kemeswaran and Addor, U.S. Pat. No. 4,046,799. The alcohols of formula II can be made as described by Malhotra and Ricks, Offenlegungsschrift No. 28 10 881 and Maeda and Hirose, CA 81 135964k and 80 59873s and references cited therein.

The thiolesters of formula (A) can be prepared by the reaction of the acid of formula I with the S-thiol corresponding to the alcohol of formula II in the presence of oxalyl chloride and dimethylaminopyridine and an organic solvent such as tetrahydrofuran or dimethylformamide.

The term "lower alkyl," wherever used in the description herein and the appended claims, refers to an alkyl group, straight or branched, having a chain length of one to eight carbon atoms.

The compounds of the present invention of formula (A) have one or more asymmetric carbon atoms. The present invention includes each of the optical isomers and racemic mixtures thereof. In the examples hereinafter, unless otherwise specified, the compound prepared in a racemic mixture.

Included within the present invention are salts of the compounds of formula A. The salts are formed from strong inorganic acids or organic acids such as hydrochloric acid, sulfuric acid, phosphoric acid, p-toluenesulfonic acid, p-benzenesulfonic acid, methanesulfonic acid, Lewis acid and the like. Many of the compounds of formula A are oils which advantageously are converted into the salt for convenience of handling and formulating and superior stability. The salts are useful for the control of pests in the same way as the compounds of formula A.

The compounds of the present invention of formula A are useful pest control agents, particularly for the control of insects and acarids. In the use of the compounds of formula A for combating insects and acarids for the protection of agricultural crops, for example soybeans, cotton, alfalfa, etc., a compound of formula A, or mixtures thereof, together with a carrier is applied to the locus in a pesticidally effective amount. The carrier can be liquid or solid and include adjuvants such as wetting agents, dispersing agents and other surface active agents. The compounds of formula A can be used in formulations such as wettable powders, solutions, dusts, granules, emulsifiable concentrates, and the like. Suitable solid carriers include natural and synthetic silicates and clays, carbon or charcoal granules, natural and synthetic resins, waxes, and the like. Suitable liquid carriers include water, aromatic hydrocarbons, alcohols, vegetable and mineral oils, ketones, and the like. The amount of a compound of formula A in the formulation can vary widely, generally within the range of about 0.01 percent to about 90.0 percent, by weight.

As shown hereinafter, the compounds of the present invention are effective on many different insects and on acarids. The compounds are effective control agents for insects such as mosquitoes, flies, aphids, weevils and acarids such as the spider mite and ticks. Depending upon the particular combination of the substituents of formula A herein, the compounds have a broad or relatively narrow spectrum of unusually high pesticidal activity on insects and acarids. Among the pests against which the compounds of the present invention are pesticidally effective are insects of the order Lepidoptera, Orthoptera, Heteroptera, Homoptera, Diptera, Coleoptera or Hymenoptera, and acarids of the order Acarina including mites of the family Tetranychidae and ticks such as Ornithodoros.

The compounds of the present invention can be used in combination with other pesticides such as the carbamates, phosphates and insect growth regulators, e.g., propoxur, carbaryl, naled, dichlorvos, phosmet, chlorpyrifos, acephate, diazinon, methoprene, kinoprene, hydroprene, cyhexatin, resmethrin, permethrin and fenvalerate.

The following examples are provided to illustrate the practice of the present invention. Temperature is given in degrees Centigrade. RT means room temperature.

EXAMPLE 1

To a stirred solution of (6-phenoxy-2-pyridyl)methanol (0.2 g, 0.99 mmol) and triethylamine (0.14 g, 1.38 mmol) in ether (about 15 ml), under nitrogen, is added by syringe a solution of the acid chloride of 2-(2-naphthyl)-3-methylbutanoic acid (1.5 mmol) in ether. The mixture is stirred for 30 minutes and then quenched with saturated aqueous sodium bicarbonate. The ether phase is washed with aqueous sodium bicarbonate, water and brine and filtered through silica. Evaporation of solvent, followed by thin layer chromatography using a circular chromatograph, eluting with 20% ether/hexane, gives (6-phenoxy-2-pyridyl)methyl 2-(2-napthyl)-3-methyl-butanoate, MS m/e 411(M+).

EXAMPLE 2

A. To a solution of 6-phenoxypyridyl-2-carboxaldehyde (0.37 g, 1.8 mmol) in 25 ml of ether is added 25 ml of water followed by sodium cyanide (0.149 g, 3.04 mmol). The mixture is stirred vigorously while a solution of sodium bisulfite (0.257 g, 2.47 mmol) in 15 ml of water is added over about 5 minutes. The reaction mixture is stirred for two hours. The organic phase is separated, washed with water, dried over calcium sulfate and solvent evaporated to give cyano(6-phenoxy-2-pyridyl)methanol.

B. To the acid chloride of 2-(2-naphthyl)-3-methylbutanoic acid (2.5 mmol) in ether is added 1.3 ml of triethylamine followed by the cyano(6-phenoxy-2-pyridyl)methanol in 5 ml of ether, from part A above, over about 2 minutes. The reaction mixture is stirred for about 18 hours and then quenched with saturated aqueous sodium bicarbonate. The organic phase is washed with aqueous sodium bicarbonate, water and brine, dried over calcium sulfate and solvent evaporated. The crude product is chromatographed on a circular chromatograph eluting with 20% ether/hexane to give cyano(6-phenoxy-2-pyridyl)methyl 2-(2-naphthyl)-3-methylbutanoate, MS m/e 436 (M+).

EXAMPLE 3

To a stirred, fully dissolved solution of cyano (6-phenoxy-2-pyridyl)methanol (170 mg, 0.832 mmol), 2-(2-naphthyl)-3-methylbutanoic acid (190 mg, 0.832 mmol) and dimethylaminopyridine (120 mg, 0.998 mmol) in 20 ml of methylene chloride and 2 ml of dimethylformamide is added N,N'-dicyclohexylcarbodiimide (170 mg, 0.832 mmol). The reaction mixture is stirred, at RT, for 13 hours and then filtered and extracted with water. The aqueous phase is extracted with ether. The combined organic phases are washed with water and brine and dried over sodium sulfate. The crude product is chromatographed on a rotary chromatograph eluting with 15% ethyl acetate/hexane to yield cyano(6-phenoxy-2-pyridyl) methyl 2-(2-naphthyl)-3-methylbutanoate.

Following the same method, (6-phenoxy-2-pyridyl) methyl 2-(2-naphthyl)-3-methylbutanoate is made from 2-(2-naphthyl)-3-methylbutanoic acid and (6-phenoxy-2-pyridyl) methanol.

EXAMPLE 4

Following the procedure of Example 3, 2-(2-naphthyl)-3-methylbutanoic acid is reacted with cyano [6-(4-fluorophenoxy)-2-pyridyl]methanol to give cyano[6-(4-fluorophenoxy)-2-pyridyl]methyl 2-(2-naphthyl)-3-methylbutanoate.

EXAMPLE 5

The acid chloride of 2-(2-naphthyl)-3-methylbutanoic acid is reacted with the alcohol in column I as in Example 2 to give the resulting ester on column II.

I cyano[6-(4-methylphenoxy)-2-pyridyl]methanol
cyano[6-(4-methoxyphenoxy)-2-pyridyl]methanol
cyano[6-(4-chlorophenoxy)-2-pyridyl]methanol
cyano[6-(4-methylthiophenoxy)-2-pyridyl]methanol
cyano[6-(4-trifluoromethylphenoxy)-2pyridyl]methanol
cyano[6-(3,4-dimethylphenoxy)-2-pyridyl]methanol
cyano[6-(2-fluorophenoxy)-2-pyridyl]methanol
cyano[6-(4-chloro-2-trifluoromethylphenoxy)-2-pyridyl]methanol.

II cyano[6-(4-methylphenoxy)-2-pyridyl]methyl 2-(2-naphthyl)-3-methylbutanoate
cyano[6-(4-methoxyphenoxy)-2-pyridyl]methyl 2-(2-naphthyl)-3-methylbutanoate
cyano[6-(4-chlorophenoxy)-2-pyridyl]methyl 2-(2-naphthyl)-3-methylbutanoate
cyano[6-(4-methylthiophenoxy)-2-pyridyl]methyl 2-(2-naphthyl)-3-methylbutanoate
cyano[6-(4-trifluoromethylphenoxy)-2-pyridyl]methyl 2-(2-naphthyl)-3-methylbutanoate
cyano[6-(3,4-dimethylphenoxy)-2-pyridyl]methyl 2-(2-naphthyl)-3-methylbutanoate
cyano[6-(2-fluorophenoxy)-2-pyridyl]methyl 2-(2-naphthyl)-3-methylbutanoate
cyano[6-(4-chloro-2-trifluoromethylphenoxy)-2-pyridyl]methyl 2-(2-naphthyl)-3-methylbutanoate

EXAMPLE 6

The acid chloride of 2-(2-naphthyl)-3-methylbutanoic acid is reacted with [6-(4-fluorophenoxy)-2-pyridyl]methanol using the procedure of Example 1 to give [6-(4-fluorophenoxy)-2-pyridyl]methyl 2-(2-naphthyl)-3methylbutanoate.

EXAMPLE 7

A. To 8.45 mmol of (6-phenoxy-2-pyridyl)methanol in 75 ml ether is added, at −10°, 12.7 mmol of phosphorus tribromide. The solution is refluxed for 1 hour, after which approximately 1 ml of phosphorus tribromide is added and refluxing is continued for 2 hours. The reaction mixture is cooled to RT and resulting solid is filtered and washed with ether to yield the hydrogen bromide salt of (6-phenoxy-2-pyridyl)methyl bromide.

B. Washed sodium hydride (1.9 mmol) in 20 ml ether is cooled to 5° and 1.9 mmol thioacetic acid is added. This solution is stirred at RT for 15 minutes, after which it is again cooled to 5° and 0.87 mmol of the bromide salt from A above is added. The solution is stirred at 5° for 10 minutes, allowed to warm to RT and stirred at RT for 2 days. The solution is brought up in ether, then washed with 5% sodium hydroxide, water (2×) and brine, and dried over sodium sulfate to give S-(6-phenoxy-2-pyridyl)methyl acetate.

C. To 15 ml ether is added lithiumaluminumhydride (1.3 mmol), followed by 0.86 mmol S-(6-phenoxy-2-pyridyl) methyl acetate at 5°. After stirring for 5 hours at RT, the solution is quenched with approximately 0.05 ml water, approximately 0.1 ml 15% sodium hydroxide and approximately 0.2 ml water. The solution is filtered through celite, then stripped of solvent, brought up carefully in 10% hydrochloric acid, extracted with ether and washed with water. The combined samples are dried over sodium sulfate, yielding (6-phenoxy-2-pyridyl)methane thiol.

EXAMPLE 8

Oxalyl chloride (1.65 mmol) and dimethylformamide are added, at RT, to 2-(2-naphthyl)-3-methylbutanoic acid (0.92 mmol) in 10 ml benzene. After all gas evolution has stopped, about 5 minutes, the solution is warmed to 40°, then stripped of solvent and excess oxalyl chloride. The residue is brought up in tetrahydrofuran, and the (6-phenoxy-2-pyridyl)methane thiol (0.92 mmol) and dimethylaminopyridine are added with stirring. Stirring is continued for 18 hours, after which the solution is brought up in ether, washed with water (3×) and brine, and dried over sodium sulfate to give S-(6-phenoxy-2-pyridyl)methyl thioester of 2-(2-naphthyl)-3-butanoic acid.

In the same manner, methyl (6-phenoxy-2-pyridyl) methane thiol and 2-(2-naphthyl)-3-methylbutanoic acid are reacted, yielding S-methyl(6-phenoxy-2-pyridyl)-methyl thioester of 2-(2-naphthyl)-3-butanoic acid.

EXAMPLE 9

To sodium hydride, 0.91 g, (22.3 mmol) (washed with hexane) is added, under nitrogen, 8 ml of tetrahydrofuran. The suspension is then cooled in an ice bath. Thiophenol (2.32 g, 21.1 mmol) in 8 ml of tetrahydrofuran is added dropwise over 30 minutes, after which 4 ml of hexamethylphosphorictriamide is added. The solution is added dropwise over 15 hr to 5 g (21.1 mmol) 2,6-dibromopyridine in 8 ml tetrahydrofuran and 2 ml hexamethylphosphorictriamide at 24°. The reaction mixture is stirred overnight under nitrogen. After addition of 2 ml hexamethylphosphorictriamide, the solution is refluxed for 3 days, then diluted with water and extracted with ether, washed with 5% sodium hydroxide (2×), water (3×) and brine, dried over magnesium sulfate and concentrated. The residue is finally washed with 100 ml cold (ice bath) hexane to give 2-bromo-6-phenylthiopyridine, m.p. 47°.

A solution of m-butyllithium (4.23 ml, 6.77 mmol) in 15 ml ether is cooled to −50°, and a solution of 1.5 g (5.64 mmol) 2-bromo-6-phenylthiopyridine in 15 ml ether is added over a period of 45 minutes at −45° to −50°. After addition, stirring is continued for 45 minutes at −40° to −50°, then the solution is cooled to −70° and separated with dry ice, followed by addition of 15 ml of 4N hydrochloric acid. The suspension is warmed to RT and solid sodium hydroxide added. The layers are separated and the ether layer extracted with saturated NaHCO₃. The aqueous layers are combined, washed with ether and acidified with conc. hydrochloric acid. The resulting precipitate is filtered, washed with water and dried in vacuo overnight, giving 6-phenylthio-2-pyridylcarboxylic acid.

To a cooled solution of 6-phenylthio-2-pyridylcarboxylic acid (0.75 g, 3.25 mmol) in 10 ml of tetrahydrofuran in an ice bath is added dropwise a borane-tetrahydrofuran solution (6.7 ml total, 6.70 mmol) over a period of 20 minutes. The reaction mixture is stirred at RT overnight. 3 N aqueous sodium hydroxide (4 ml) is added slowly and stirring is continued for another 8 hours. The solution is diluted with water, saturated with solid potassium carbonate and extracted with water. The extract is washed with water, saturated NaHCO₃ and brine and dried to yield (6-phenylthio-2-pyridyl)methanol.

Following the procedure of Example 3, (6-phenylthio-2-pyridyl)methanol and 2-(2-naphthyl)-3-methylbutanoic acid are reacted to give (6-phenylthio-2-pyridyl)methyl 2-(2-naphthyl)-3-methylbutanoate.

EXAMPLE 10

Following the procedure of Example 3, each of methyl (6-phenoxy-2-pyridyl)methanol and methyl[6-(4-fluorophenoxy)-2-pyridyl]methanol is reacted with 2-(2-naphthyl)-3-methyl-butanoic acid to yield methyl (6-phenoxy-2-pyridyl) methyl 2-(2-naphthyl)-3-methylbutanoate and methyl[6-(4-fluorophenoxy)-2-pyridyl]-methyl 2-(2-naphthyl)-3-methylbutanoate, respectively.

Further, ethynyl(6-phenoxy-2-pyridyl)-methyl 2-(2-naphthyl)-3-methylbutanoate is made from 2-(2-naphthyl)-3-methylbutanoic acid and ethynyl(6-phenoxy-2-pyridyl)methanol.

EXAMPLE 11

To 15 g of 6-methyl-2-pyridylcarboxylic acid (122 mmol) in 200 ml benzene is added dropwise 19.1 g (150 mmol) oxalyl chloride (dissolved in 30 ml benzene) with ice bath cooling. The solution is allowed to come to RT and is stirred 1 hour, after which it is stripped, 100 ml of benzene is added, and it is stripped again. The residue is taken up in 200 ml benzene and 41 g of aluminumtrichloride (310 mmol) is added in portions over a 3 hour period with ice bath cooling. The solution is heated to 25° for 1 hour, then heated to reflux for 2 hours, and finally cooled and stirred overnight. The mixture is poured onto ice/conc. HCl, then washed with ether. Fifty Percent (50%) sodium hydroxide is added until the precipitate is dissolved. The solution is extracted with CHCl₃, washed with water, dried and stripped, leaving 6-benzoyl-2-methylpyridine.

The 6-benzoyl-2-methylpyridine (3.9 g, 21 mmol), in 20 ml CHCl₃, is added over 1 hour to 4.2 g (21 mmol) m-chloroperbenzoic acid (in 50 ml CHCl₃). The temperature is kept below 25° as the mixture is stirred overnight. The reaction is diluted with CHCl₃, washed with sat. NaHSO₃, water, 20% NaHCO₃ (2×) and then water, dried, stripped and finally titrated with hexane/ethyl acetate to give 6-benzoyl-2-methylpyridine N-oxide.

Acetic anhydride (6.6 ml) is heated to 115°, after which 6-benzoyl-2-methylpyridine N-oxide is added in portions over 1 hour. The mixture is then held at 115° for 1 hour after the addition. The reaction is poured onto ice and extracted with ether (3×). The combined ether phases are washed with sat. NaHCO₃ (2×) and water until neutral, dried and stripped. The product is preparatory thin layer chromatographed, the least polar band giving 2-(acetoxymethyl)-6-benzoylpyridine.

Potassium hydroxide (1.1 g, 18 mmol) is dissolved in 25 ml methanol, after which is added 2-(acetoxymethyl)-6-benzoylpyridine (2.3 g, 9 mmol) in 20 ml methanol and the mixture is then stirred overnight. The mixture is diluted with water and saturated sodium chloride, then extracted with ether (2×), washed with sat. sodium chloride, dried over magnesium sulfate and stripped to yield (6-benzoyl-2-pyridyl)methanol.

Following the procedure of Example 3, (6-benzoyl-2-pyridyl)methanol and 2-(2-naphthyl)-3-methylbutanoic acid are reacted, yielding (6-benzoyl-2-pyridyl)methyl 2-(2-naphthyl)-3-methylbutanoate.

EXAMPLE 12

A. To a cooled solution, about 5°, of 2-(2-naphthyl)-3-methylbutanoic acid (3.38 mmol) in 25 ml of dimethylformamide is added triethylamine (3.38 mmol) and ethyl chloroformate (3.38 mmol). The reaction mixture is stirred for about 15 minutes and then sodium hydrosulfide (6.76 mmol) and 10 ml of dimethylformamide are added. The mixture is stirred at 5° for about 1.5 hours. The reaction is worked up by adding ether and then acidifying with 5% $H_2SO_4$. The ether layer is washed with water and brine, dried over sodium sulfate and solvent evaporated to give the thioacid of 2-(2-naphthyl)-3-methylbutanoic acid.

B. To 15 ml of dimethylformamide and 10 ml of tetrahydrofuran is added 1.60 mmol of the thioacid of part A, $KHCO_3$ (4.01 mmol) and the mesylate of α-cyano-(6-phenoxy-2-pyridyl)methanol (1.60 mmol). The reaction mixture is stirred at RT for about 18 hours. The mixture is taken up in ether, washed with water and brine, dried over sodium sulfate and solvent stripped to give S-α-cyano-(6-phenoxy-2-pyridyl)methyl thioester of 2-(2-naphthyl)-3-methylbutanoic acid.

EXAMPLE 13

A mixture of (6-benzoyl-2-pyridyl)methanol (1.5 g, 7 mmol), potassium hydroxide (1.3 g, 23 mmol) and hydrazine 85% (1 ml, 25 mmol) in triethylene glycol (10 ml) is refluxed for 1.5 hours, and then the water and excess hydrazine are removed by a takeoff condenser until the temperature rises to 195°–200°. After 4 hours at 195°–200°, the solution is cooled, poured into ice and water (50 ml) and extracted with ether (3×20 ml). The combined ether layers are washed with water (3×20 ml), brine (10 ml) and dried over calcium sulfate. Removal of solvents gives (6-benzyl-2-pyridyl)methanol.

Following the procedure of Example 1, the acid chloride of 2-(2-naphthyl)-3-methylbutanoic acid is reacted with (6-benzyl-2-pyridyl)methanol to yield (6-benzyl-2-pyridyl)methyl 2-(2-naphthyl)-3-methylbutanoate.

Two groups of 10 each of 0–24 l hour III instar *Heliothis virescens* larvae were treated with 1 μl of the compound, cyano(6-phenoxy-2-pyridyl)methyl 2-(2-naphthyl)-3-methylbutanoate, in acetone at five different concentrations by application to the dorsum of the thorax. Two groups of 10 each are treated identically with 1 μl acetone only as controls. Larvae are held individually in 30 ml plastic cups provided with artificial medium for 72 hours at 25° and 16 hr photo-period. After 72 hr the number of dead is calculated as a percentage of the total number originally treated and then corrected for any mortality in the control groups using Abbott's formula. The $LD_{50}$ of the compound was less than 0.1%.

What is claimed is:

1. A compound of the formula:

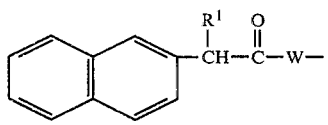

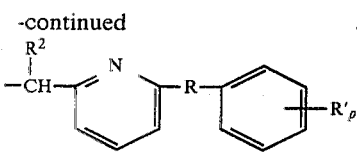

wherein,
R is oxygen, sulfur, methylene or carbonyl;
R' is fluoro, bromo, chloro, trifluoromethyl, methyl, methoxy or methylthio;
p is zero, one or two;
W is oxygen or sulfur;
$R^1$ is lower alkyl of 2 to 5 carbon atoms; and
$R^2$ is hydrogen, cyano, ethynyl, methyl or trifluoromethyl.

2. A compound according to claim 1 of the formula:

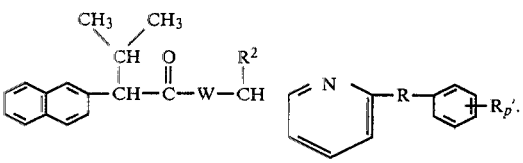

3. A compound according to claim 2 wherein $R^2$ is hydrogen, cyano or methyl.

4. A compound according to claim 3 wherein p is zero or one.

5. A compound according to claim 4 wherein W is oxygen.

6. A compound according to claim 5 wherein R is oxygen.

7. A compound according to claim 6 wherein R' is fluoro.

8. A compound according to claim 5 wherein R is carbonyl.

9. A compound according to claim 8 wherein R' is fluoro.

10. A compound according to claim 4 wherein W is sulfur.

11. A compound according to claim 10 wherein R is oxygen and R' is fluoro.

12. A compound according to claim 11 wherein $R^2$ is hydrogen.

13. A compound according to claim 10 wherein R is carbonyl and R' is fluoro.

14. A compound according to claim 13 wherein $R^2$ is hydrogen.

15. A compound according to claim 6 wherein p is zero.

16. The compound according to claim 15 wherein $R^2$ is cyano.

17. The compound according to claim 15 wherein $R^2$ is hydrogen.

18. A process for the control of pests selected from insects of the order Lepidoptera, Orthoptera, Heteroptera, Homoptera, Diptera, Coleoptera and Hymenoptera; mites of the family Tetranychidae; and ticks of the family Ornithodoros which comprises applying to the locus of the pest a compound according to claim 1, in a pesticidally effective amount, and a suitable liquid or solid carrier.

19. The process of claim 18 wherein the compound is a compound according to claim 6.

20. The process of claim 18 wherein the compound is a compound according to claim 17.

21. The process according to claim 20 wherein the pest is an insect of the order Lepidoptera.

* * * * *